United States Patent [19]

Ahlert et al.

[11] Patent Number: 5,423,337
[45] Date of Patent: Jun. 13, 1995

[54] MEDICATED DENTAL FLOSS

[76] Inventors: Gary Ahlert, 135—178 Dearborn Ave., Rye, N.Y. 10580; Scott Evert, 4463 Rudy Rd., Tipp City, Ohio 45371

[21] Appl. No.: 217,602

[22] Filed: Mar. 24, 1994

[51] Int. Cl.$^6$ .................... A61C 15/00; A61C 5/00; A61F 13/00; A61K 33/4
[52] U.S. Cl. ..................... 132/321; 424/401; 424/490; 424/495; 424/53; 424/616
[58] Field of Search .................. 132/321; 424/53, 616, 424/490, 495

[56] References Cited

U.S. PATENT DOCUMENTS

| | | | |
|---|---|---|---|
| 3,830,247 | 8/1974 | Kaphalakos | 132/90 |
| 4,175,326 | 11/1979 | Goodson | 433/80 |
| 4,293,426 | 10/1981 | Gago | 210/759 |
| 4,421,669 | 12/1983 | Brichard | 252/186.25 |
| 4,470,839 | 9/1984 | Gago | 71/34 |
| 4,892,736 | 1/1990 | Goodson | 424/435 |
| 4,922,935 | 5/1990 | Birkeland | 132/309 |
| 4,963,327 | 10/1990 | Russell | 422/120 |
| 4,980,154 | 12/1990 | Gordon | 424/53 |
| 4,986,288 | 1/1991 | Kent et al. | 132/321 |
| 5,065,861 | 11/1991 | Greene et al. | 132/325 |
| 5,125,834 | 6/1992 | Swan | 433/80 |
| 5,129,824 | 7/1992 | Keller | 433/215 |
| 5,209,251 | 5/1993 | Curtis et al. | 132/321 |
| 5,310,563 | 5/1994 | Curtis et al. | 424/616 |
| 5,330,357 | 7/1994 | Keller | 132/321 |

FOREIGN PATENT DOCUMENTS

| | | |
|---|---|---|
| 358363A | 3/1990 | European Pat. Off. |
| 2024630 | 1/1980 | United Kingdom |
| 2189398 | 10/1987 | United Kingdom |
| 9114412 | 3/1990 | WIPO |
| 9111970 | 8/1991 | WIPO |
| 9200718 | 1/1992 | WIPO |

*Primary Examiner*—Shep K. Rose
*Attorney, Agent, or Firm*—Patrick J. Walsh

[57] ABSTRACT

Dental floss having a wax or similar caoting impregnated with a nascent oxygen generating agent such as calcium peroxide.

8 Claims, No Drawings

MEDICATED DENTAL FLOSS

FIELD OF THE INVENTION

The present invention relates to the treatment of teeth and gums and particularly to enabling an individual to provide improved dental hygiene in applying dental floss bearing an antibacterial agent.

BACKGROUND OF THE INVENTION

There are areas of the mouth, in particular the spaces between the teeth, that are not normally reached by brushing and as a result do not receive the benefit of therapeutic agents as are applied to the open surfaces of the teeth. As a result, dental floss is commonly used to augment dental hygiene so that by the mechanical action of the dental floss the interproximal surfaces of the teeth are cleaned.

Dental floss typically comprises wax or other polymer coated thread manufactured by applying hot coating to the thread. It is known to include therapeutic agents in dental floss for release from the floss to interproximal surfaces of the teeth by the action of flossing.

Oxygen generation is known to have germicidal activity in the mouth. In particular, it has long been known that certain compositions such as baking soda and hydrogen peroxide provide highly effective cleaning action on the teeth. Peroxides are known to release nacsent oxygen in the aqueous environment of the mouth and are recommended for brushing the teeth in order to attain the desired germicidal action on oral bacteria.

The application of therapeutic agents such as oxygen generating peroxides has heretofore not been possible in conventional dental floss because of decomposition of the peroxide at the elevated temperature of the wax coating in manufacture. Additionally, peroxide components cannot be added to dental floss by other known aqueous coating techniques because the peroxide component decomposes when exposed to water.

SUMMARY OF THE INVENTION

The present invention comprises a dental floss in which a nascent oxygen generating antibacterial agent is embedded in the dental floss strip for release by the mechanical forces encountered while flossing, or by enzymatic release.

In a preferred form, dental floss according to the invention comprises a wax or other polymer coated filament having an active ingredient such as calcium peroxide in microencapsulation, and with the microencapsulated calcium peroxide distributed through the wax coating.

An advantage of microencapsulating is that the active ingredient maintains its efficacy from the time of manufacture until use when the active ingredient is released by the mechanical or enzymatic action of applying the floss between the teeth. In the case of calcium peroxide, the flossing action releases the ingredient between the teeth and below the gum line while the calcium peroxide in the aqueous environment of the mouth releases nascent oxygen as a germicide.

OBJECTS OF THE INVENTION

It is an object of the invention to provide dental floss with an encapsulated active ingredient for therapeutic use.

It is an object of the invention to deliver therapeutic agents such as calcium peroxide to the mouth that are not achieved by conventional methods.

Another object of the invention is to provide encapsulation for stabilizing and preserving the potency of active therapeutic ingredients lodged in dental floss for release when the floss in used.

Other and further objects of the invention will occur to one skilled in the art with an understanding of the following detailed description of the invention or upon employment of the invention in practice.

DETAILED DESCRIPTION OF THE INVENTION

The present invention may be use with dental floss of varying configurations and materials as are known including monoand multi-filament designs coated with wax or other coating material.

In accordance with the invention, a nascent oxygen generating active ingredient is encapsulated by means of microencapsulation techniques into small beads. Suitable encapsulation materials include ethylcellulose and other coating polymers which coat and preserve the active ingredient until release by mechanical action of flossing between teeth and by enzymatic action especially interaction of calcium peroxide and saliva or water in the mouth for generation nascent oxygen for germicidal action at interproximal spaces.

In a preferred method of manufacture of the invention, the nascent oxygen generating active ingredient preferably calcium peroxide is preferably microencapsulated in a suitable coating such as ethylcellulose with approximately 50% to 99% of coating weight per unit weight of calcium peroxide. Next, the encapsulated calcium peroxide is evenly mixed with a suitable floss coating such as hot microcrystalline wax or polyethylene glycol with up to 30% weight of encapsulated calcium peroxide per unit weight of floss coating. The wax mixture coating is applied to the floss by known techniques of drawing the floss through the hot mixture. In manufacture, an even distribution of the microcapsules through the the wax coating is maintained during mixture and coating of the thread so that the active ingredient is evenly distributed along the length of the finished floss.

In accordance with the invention, microencapsulation insulates the calcium peroxide from heat degradation when mixed with the hot floss coating, preserves the integrity of the calcium peroxide in the floss coating for extended shelf life, and is readily released in use primarily by the mechanical action of breaking the microcapsules for release of the calcium peroxide at the interproximal surfaces, and secondarily by the enzymatic action of saliva and water in the mouth in the presence of the calcium peroxide. Calcium peroxide in the aqueous environment of the mouth generates nascent oxygen for germicidal action.

We claim:

1. Dental floss comprising a thread, a floss coating on the thread, microencapsulated calcium peroxide embedded in the floss coating and evenly distributed along the coated floss so that the microencapsulation breaks by mechanical action in use to release the calcium peroxide for generating nascent oxygen at interproximal surfaces of the teeth, the microencapsulated calcium peroxide comprising up to 30% by weight of the floss coating, and the microencapsulation coating comprises approximately 50% to 99% by weight of calcium peroxide.

2. Dental floss as defined in claim 1 in which the floss coating is microcrystalline wax.

3. Dental floss as defined in claim 1 in which the floss coating is polyethylene glycol.

4. A method of fabricating dental floss comprising the steps of microencapsulating calcium peroxide in a coating with approximately 50% to 99% of coating weight per unit weight of calcium peroxide, mixing the encapsulated calcium peroxide with a floss coating selected from the group consisting of hot microcrystalline wax and polyethylene glycol with up to 30% weight of microencapsulated calcium peroxide per unit weight of floss coating, applying the coating mixture to the floss by drawing the floss through the hot mixture, and maintaining an even distribution of the microcapsulated calcium peroxide through the floss coating during mixture and coating of the floss so that the calcium peroxide is evenly distributed along the length of the finished floss.

5. A method as defined in claim 4 in which the calcium peroxide is encapsulated in ethyl cellulose.

6. Dental floss produced by the method comprising the steps of microencapsulating calcium peroxide in a coating with approximately 50% to 99% of coating weight per unit weight of calcium peroxide, mixing the encapsulated calcium peroxide with a floss coating selected from the group consisting of hot microcrystalline wax and polyethylene glycol with up to 30% weight of microencapsulated calcium peroxide per unit weight of floss coating, applying the coating mixture to the floss by drawing the floss through the hot mixture, and maintaining an even distribution of the microcapsulated calcium peroxide through the floss coating during mixture and coating of the floss so that the calcium peroxide is evenly distributed along the length of the finished floss.

7. Dental floss produced in claim 6 in which the calcium peroxide is microencapsulated in ethyl cellulose.

8. Dental floss as defined in claim 1 in which the calcium peroxide is microencapsulated by ethyl cellulose.

* * * * *